(12) United States Patent
Hirose

(10) Patent No.: US 8,472,028 B2
(45) Date of Patent: Jun. 25, 2013

(54) OPTICAL COHERENCE TOMOGRAPHIC APPARATUS

(75) Inventor: Futoshi Hirose, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 686 days.

(21) Appl. No.: 12/241,810

(22) Filed: Sep. 30, 2008

(65) Prior Publication Data

US 2009/0091766 A1 Apr. 9, 2009

(30) Foreign Application Priority Data

Oct. 4, 2007 (JP) ................................. 2007-260855

(51) Int. Cl.
*G01B 11/02* (2006.01)
(52) U.S. Cl.
USPC ......................................................... 356/497
(58) Field of Classification Search
USPC .................... 356/479, 497, 511, 512; 600/425
See application file for complete search history.

(56) References Cited

U.S. PATENT DOCUMENTS

| | | | | |
|---|---|---|---|---|
| 6,137,585 A | 10/2000 | Hitzenberger et al. | ....... | 356/484 |
| 6,288,784 B1 | 9/2001 | Hitzenberger et al. | ....... | 356/485 |
| 6,307,634 B2 | 10/2001 | Hitzenberger et al. | ....... | 356/484 |
| 7,400,410 B2* | 7/2008 | Baker et al. | ................... | 356/498 |
| 2005/0140981 A1* | 6/2005 | Waelti | ........................... | 356/479 |
| 2008/0285043 A1* | 11/2008 | Fercher et al. | ................ | 356/451 |

FOREIGN PATENT DOCUMENTS

| | | |
|---|---|---|
| EP | 1 582 143 A1 | 10/2005 |
| EP | 1 780 530 A1 | 5/2007 |
| JP | 2002-515593 A | 5/2002 |
| WO | WO 99/60331 | 11/1999 |
| WO | WO 00/28885 | 5/2000 |
| WO | 2007-065670 | 6/2007 |
| WO | WO 2007/065670 A2 | 6/2007 |

OTHER PUBLICATIONS

Official Letter/Search Report, dated Jan. 19, 2009, issued by the European Patent Office, in European Application No. 08017195.2.

* cited by examiner

*Primary Examiner* — Tarifur Chowdhury
*Assistant Examiner* — Jonathan Hansen
(74) *Attorney, Agent, or Firm* — Fitzpatrick, Cella, Harper & Scinto

(57) ABSTRACT

An optical coherence tomographic apparatus wherein a reference light path includes at least a first reference light path and a second reference light path having an optical path length shorter than that of the first reference light path, wherein first tomographic information of the object at a first inspection position based on the optical interference using the first reference light path and second tomographic information of the object at a second inspection position based on the optical interference using the second reference light path, are acquired, the second inspection position being shallower than the first inspection position with respect to a depth direction of the object, and wherein a positional deviation a tomographic image at the first inspection position obtained based on the first tomographic information is corrected using the second tomographic information.

25 Claims, 4 Drawing Sheets

OPTICAL COHERENCE TOMOGRAPHIC APPARATUS

FIELD OF THE INVENTION AND RELATED ART

This invention relates to an optical coherence tomographic apparatus (tomograph). More particularly, the present invention concerns an optical coherence tomographic apparatus having an interference optical system and used for ophthalmologic examination and treatment, for example.

There are a wide variety of ophthalmologic equipments using an optical instrument. For example, there are various optical instruments for observing eyes, such as a front eye part photographic apparatus, a retinal camera, a confocal laser scan ophthalmoscope (Scanning Laser Ophthalmoscope: SLO) and so on.

Particularly, an optical coherence tomographic apparatus (Optical Coherence Tomography: OCT) (hereinafter, "OCT apparatus") is an apparatus which is designed to acquire a tomogram of a sample at high resolution. Currently, this apparatus is ophthalmologic equipment indispensable for the retina-specialized outpatient medical treatment.

The OCT apparatus operates in the following principle. First of all, a low coherent light emitted from a light source is split into a reference light and a measuring light. The reference light is reflected by a reference mirror. The measuring light is projected to a sample, and it is reflected by the sample. The light reflected by the reference mirror and the light reflected by the sample are caused to interfere with each other. Based on the thus produced interference light, the OCT apparatus acquires a tomogram of the sample at high resolution.

It is to be noted that the tomogram of the sample is obtained by the OCT apparatus by projecting the measuring light onto the sample while being scanned.

Since a tomogram of the retina at the eyeground to be examined can be photographed at high resolution by this OCT apparatus, it is utilized widely in the retina ophthalmologic diagnoses.

By the way, the eyeball of human being has involuntary eye motion, called flicks. Therefore, when the OCT apparatus is used for retina ophthalmologic diagnoses and if the time to be taken to acquire the retina tomogram is long, there will be a large influence on positional deviation between images due to the eyeball motion during the measurement. This may cause a disturbance of the image in the retina tomogram, called "motion artifact".

Conventionally, patent document 1 discloses an OCT apparatus for eyeground observation which uses a Mach-Zehnder interference system to avoid the above-described motion artifact. This OCT apparatus is arranged so that the measuring light is incident on the retina which is a portion of the eyeball to be examined, while being scanned. On the other hand, the reference light is defined while the corneal surface which is a portion of the eyeball functions like a mirror which is a component of the optical system.

Namely, the apparatus is arranged so that, by defining a reference light path while the cornea functions like a mirror as described above, the motion artifact to the retina tomogram due to the motion of the eyeball during the measurement is reduced.

[Patent Document 1]
Japanese Published Patent Application No. JP 2002-515593A, FIG. 2

Although the patent document 1 attempted to reduce the aforementioned motion artifact, in OCT apparatuses such as described above further improvements are still desired to reduce the motion artifact on one hand and to achieve enhancement of the resolution on the other hand.

In view of the foregoing, the present invention provides an optical coherence tomographic apparatus (OCT apparatus) which can reduce the motion artifact particularly when a tomogram of a retina at the eyeground of the eye to be examined is photographed.

In accordance with an aspect of the present invention, there is provided an optical coherence tomographic apparatus wherein light from a light source is split into a measuring light and a reference light, wherein the measuring light is projected onto an object to be inspected, through a measurement light path, wherein a returning light of the measuring light coming back from the object to be inspected is directed toward a detection position, wherein the reference light is directed toward the detection position through a reference light path so that the reference light optically interferes with the returning light directed to the detection position, and wherein a tomographic image of the object to be inspected is obtained using a signal based on the optical interference, characterized in that: the reference light path includes at least a first reference light path and a second reference light path having an optical path length shorter than that of the first reference light path; said apparatus is configured to acquire first tomographic information of the object at a first inspection position based on the optical interference using the first reference light path and second tomographic information of the object at a second inspection position based on the optical interference using the second reference light path, the second inspection position being shallower than the first inspection position with respect to a depth direction of the object; and said apparatus is configured to correct a positional deviation of a tomographic image at the first inspection position obtained based on the first tomographic information, using the second tomographic information.

The optical coherence tomographic apparatus may further comprise reference optical path length control means configured to independently control reference optical path lengths of the first reference light path and the second reference light path.

The reference optical path length control means may adjust the reference optical path lengths of the first reference light path and the second reference light path so that the first tomographic information and the second tomographic information are separated from each other with respect to time.

The adjustment by said reference optical path length control means may be performed automatically.

The optical coherence tomographic apparatus may further comprise detecting means configured to detect a light intensity at the detection position and to convert it into an electrical signal, so as detect a signal based on the optical interference, and image forming means configured to perform arithmetic operation to the electrical signal to obtain an image.

At least one of the first reference light path and the second reference light path may be provided with dispersion compensation means.

In the optical coherence tomographic apparatus, as the first tomographic information, a first reference optical system for acquiring a retina tomographic image of an eye to be examined may be comprised of the first reference light path and, as the second tomographic information, a second reference optical system for acquiring a cornea tomographic image of the eye to be examined may be comprised of the second reference light path, wherein, when the retina tomographic image is made, a positional deviation of the retina tomographic image may be corrected based on the second tomographic information including information about the position of the cornea, thereby to reduce motion artifact.

The first reference light path and the second reference light path may have an optical path length difference of not less than 30 mm and not greater than 60 mm.

The first reference light path constituting the first reference optical system may be provided with dispersion compensation means configured to compensate ophthalmic dispersion of the eye to be examined.

The optical coherence tomographic apparatus may further comprise an inspection optical system configured to direct a returning light from the object to be inspected toward the detection position, a detection optical system configured to direct the measuring light toward the object to be inspected, through the measurement light path, and a reference optical system configured to direct the reference light toward the detection position, wherein a light path of at least one of said inspection optical system, said detection optical system and said reference optical system may be comprised of an optical fiber.

In accordance with another aspect of the present invention, there is provided an optical coherence tomographic apparatus wherein light from a light source is split into a measuring light and a reference light, wherein the measuring light is projected onto an object to be inspected, through a measurement light path, wherein a returning light of the measuring light coming back from the object to be inspected is directed toward a detection position, wherein the reference light is directed toward the detection position through a reference light path so that the reference light optically interferes with the returning light directed to the detection position, and wherein a tomographic image of the object to be inspected is obtained using a signal based on the optical interference, characterized in that: the reference light path includes at least a first reference light path and a second reference light path having an optical path length shorter than that of the first reference light path; said apparatus is configured to acquire first tomographic information of the object at a first inspection position based on the optical interference using the first reference light path, and second tomographic information of the object at a second inspection position based on the optical interference using the second reference light path, the second inspection position being shallower than the first inspection position with respect to a depth direction of the object; and the first tomographic information and the second tomographic information are related with each other with respect to a positional relationship in the depth direction.

The positional relationship in the depth direction between the first tomographic information and the second tomographic information may correspond to a positional relationship between the first inspection position and the second inspection position with respect to the depth direction.

With respect to the positional relationship in the depth direction, a positional deviation occurring in a tomograph or a three-dimensional image of the object to be examined which comprises the first tomographic information and the second tomographic information, may be corrected based on the second tomographic information.

In the optical coherence tomographic apparatus, a tomograph or a three-dimensional image of the object to be inspected in the depth direction may be produced, with the positional deviation of the second tomographic information in the depth direction being compensated, based on information about said second inspection position.

In accordance with a further aspect of the present invention, there is provided an optical coherence tomographic apparatus wherein light from a light source is split into a measuring light and a reference light, wherein the measuring light is projected onto an object to be inspected, through a measurement light path, wherein a returning light of the measuring light coming back from the object to be inspected is directed toward a detection position, wherein the reference light is directed toward the detection position through a reference light path so that the reference light optically interferes with the returning light directed to the detection position, and wherein a tomographic image of the object to be inspected is obtained using a signal based on the optical interference, characterized in that: the reference light path includes at least a first reference light path and a second reference light path having an optical path length shorter than that of the first reference light path; reference optical path length control means is configured to independently control reference optical path lengths of the first reference light path and the second reference light path; detecting means is configured to detect a light intensity at the detection position and to convert it into an electrical signal, so as detect a signal based on the optical interference; image forming means is configured to perform arithmetic operation to the electrical signal to obtain an image; said apparatus is configured to acquire first tomographic information of the object at a first inspection position based on the optical interference using the first reference light path and second tomographic information of the object at a second inspection position based on the optical interference using the second reference light path, the second inspection position being shallower than the first inspection position with respect to a depth direction of the object; said apparatus is configured to correct a positional deviation of a tomographic image at the first inspection position obtained based on the first tomographic information, using the second tomographic information; said reference optical path length control means automatically adjusts the reference optical path lengths of the first reference light path and the second reference light path so that the first tomographic information and the second tomographic information are separated from each other with respect to time; and the first reference light path and the second reference light path have an optical path length difference of not less than 30 mm and not greater than 60 mm.

Briefly, in accordance with the present invention, an optical coherence tomographic apparatus (OCT apparatus) is realized by which, when a retina tomogram at the eyeground of an eye to be examined is taken, the motion artifact is reduced and the resolution is improved significantly.

These and other objects, features and advantages of the present invention will become more apparent upon a consideration of the following description of the preferred embodiments of the present invention taken in conjunction with the accompanying drawings.

DESCRIPTION OF THE PREFERRED EMBODIMENTS

Preferred embodiments of the present invention will now be described with reference to the attached drawings.

Figure 1:
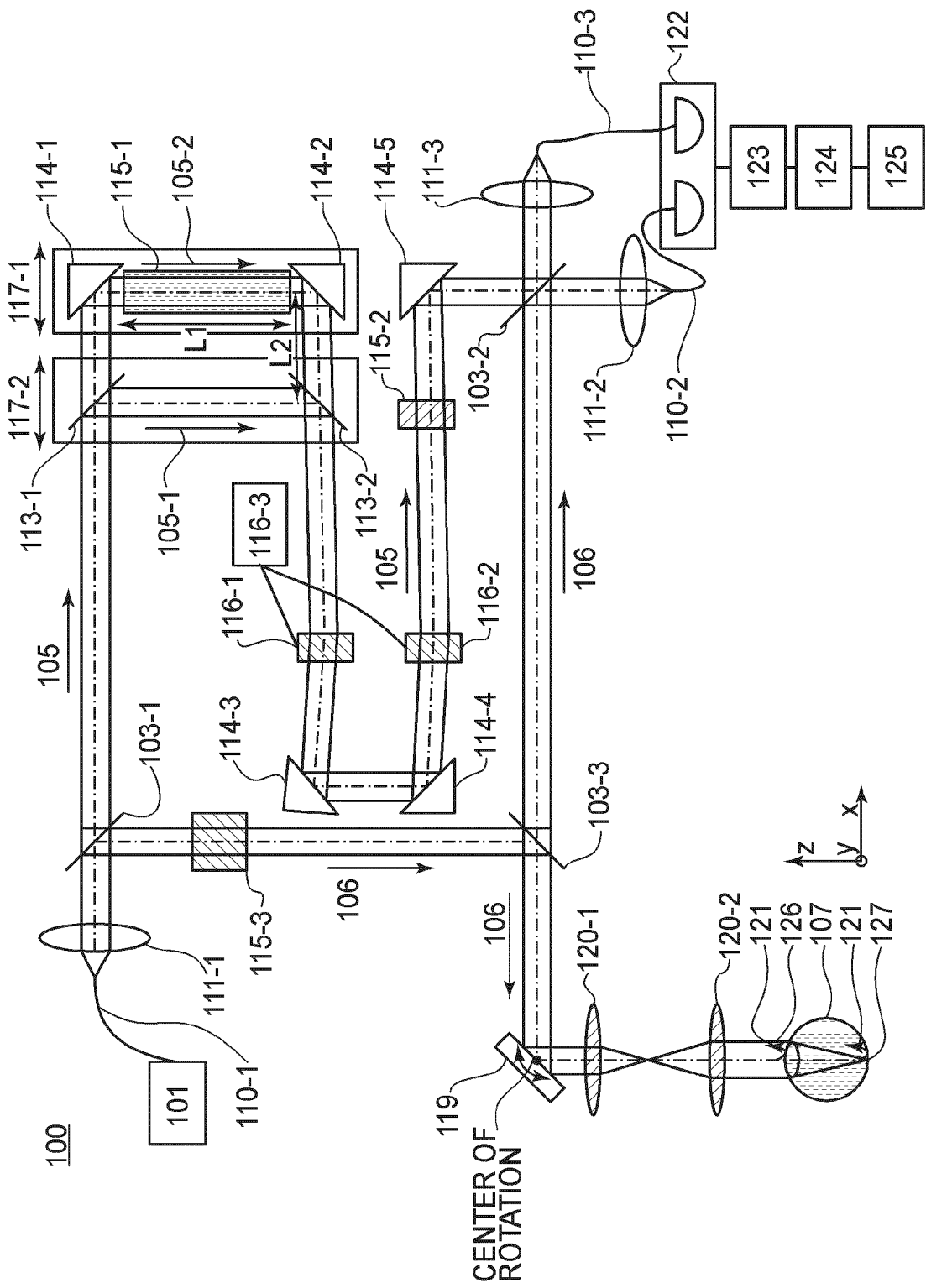
FIG. 1 is a schematic diagram for explaining an optical system of an OCT apparatus according to a first working example of the present invention.

Referring first to FIG. 1, an optical coherence tomographic apparatus (OCT apparatus) according to one preferred embodiment of the present invention will be explained. FIG. 1 is a schematic diagram for explaining an OCT apparatus according to this embodiment of the present invention. It is to be noted here that the OCT apparatus of the present invention is not limited to the one disclosed in this embodiment.

In the OCT apparatus according to the present embodiment, light from a light source 101 is split into a measuring light 106 and a reference light 105. The measuring light 106 is projected onto an object 107 to be inspected through a measurement light path (a light path along which the measuring light 106 advances). Also, a returning light of the measuring light 106 coming back from the object 107 to be inspected 107 is directed toward a detection position. Here, the returning light is a reflected light and/or a scattered light which contains information about the interface in the direction of projection of the light onto the object 107 to be inspected 107, for example.

Then, like an ordinary OCT apparatus, the reference light 105 is directed toward the detection position through a reference light path (a light path along which the reference light 105 advances), so that it optically interferes with the returning light directed to the detection position. Thus, a tomographic image of the object 107 to be inspected is photographed using a signal based on the optical interference.

An important feature of the present invention is that the reference light path includes at least a first reference light path (a light path along which the reference light 105-2 advances) and a second reference light path (a light path along which the reference light 105-1 advances), the second reference light path having an optical path length shorter than that of the first reference light path.

Using the first reference light path, first tomographic information (e.g., boundary 128-1 in FIG. 3A) at a first inspection position (e.g., retina 127) of the object to be inspected, to be acquired based on the optical interference, is acquired.

Furthermore, using the second reference light path, second tomographic information (e.g., boundary 129-1 in FIG. 3A) at a second inspection position (e.g., cornea 126) is acquired based on the optical interference. The second inspection position is shallower than the first inspection position with respect to the depth direction of object 107 to be inspected.

By acquiring a plurality of the first tomographic information while changing the incidence position of the measuring light 106 upon the object 107 to be inspected, a tomographic image as the object to be inspected is sliced along a predetermined plane is acquired.

After having acquired a plurality of the first tomographic information, tomograms or three-dimensional images provided from the plural tomographic information are jointed together, whereby a tomographic image is obtained.

Here, if the object to be inspected shifts during the measurement, a tomographic image being affected by such movement (e.g., at 330 in FIG. 3A) will be produced.

In the OCT apparatus of the present embodiment, in consideration of this, a positional deviation of a tomographic image at the first inspection position obtained based on the first tomographic information is corrected based on the second tomographic information.

Furthermore, the OCT apparatus of the present embodiment may have such structure that the first tomographic information and the second tomographic information are related with each other with respect to the positional relationship in the depth direction of the object 107 to be inspected.

Here, the positional deviation refers to a positional deviation from a tomographic image at the first inspection position which image is to be acquired if the object 107 to be inspected is held stationary during the measurement.

The correction mentioned above is based on that, even if the object 107 to be inspected displaces, the relative positional relationship between the first inspection position (e.g., retina 127) and the second inspection position (e.g., cornea 126) is substantially unchanged.

The OCT apparatus according to the present embodiment may be provided with a delay light path (reference light path) for acquiring tomographic information at the first inspection position and the second inspection position, respectively. In that occasion, tomographic information at both of these positions can be acquired sequentially. Due to the movement of the object to be inspected, the practical inspection position will deviate.

In the OCT apparatus according to the present embodiment, the first and second tomographic information is reconstructed while correcting the tomographic image formed by the first tomographic information, using the second tomographic information as a reference, for example. By this, a tomographic image (e.g., at 331 in FIG. 3B) in which the displacement of the object to be inspected is cancelled is obtained.

Here, the first reference light path and the second reference light path may preferably have a reference optical path length control means which controls the reference optical path lengths of them independently of each other. In that occasion, if the interference signals at the first inspection position and the second inspection position overlap with respect to the time base, these interference signals can be separated by changing the reference optical path length.

It is to be noted that, as long as the first and second reference light paths can be controlled independently, it is not always necessary to make both of these reference light paths variable. Only one may be made variable.

Furthermore, by use of the reference optical path length control means, the reference optical path lengths of the first reference light path and the second reference light path may desirably be adjusted so that the first tomographic information and the second tomographic information are separated from each other with respect to time. By separating the first tomographic information and the second tomographic information with respect to time, as described above, reduction of the motion artifact will be easier.

Furthermore, such adjustment may preferably be performed automatically. This enables assured separation of the first tomographic information and the second tomographic information.

Inside the OCT apparatus or in an external unit connected thereto, a detecting means for detecting the light intensity at the detection position and for converting it into an electrical signal, so as to detect a signal based on the optical interference between the measuring light and the reference light, as well as image-forming means for performing arithmetical operation to the electrical signal to obtain an image, may be provided.

Furthermore, at least one of the first reference light path and the second reference light path may preferably be provided with dispersion compensation means.

As the first tomographic information, a first reference optical system for acquiring a retina tomographic image of an eye to be examined may be comprised of the first reference light path. On the other hand, as the second tomographic information, a second reference optical system for acquiring a cornea tomographic image of the eye to be examined may be comprised of the second reference light path. With this arrangement, when the retina tomographic image is made, a positional deviation of the retina tomographic image can be corrected based on the second tomographic information including information about the position of the cornea, thereby to reduce motion artifact.

The first reference light path and the second reference light path may preferably have an optical path length difference of not less than 30 mm and not greater than 60 mm.

The first reference light path constituting the first reference optical system may preferably be provided with dispersion compensation means configured to compensate ophthalmic dispersion of the eye to be examined.

The optical coherence tomographic apparatus according this embodiment may include an inspection optical system configured to direct a returning light from the object to be inspected toward the detection position, a detection optical system configured to direct the measuring light toward the object to be inspected, through the measurement light path, and a reference optical system configured to direct the reference light toward the detection position. The light path of at least one of the inspection optical system, detection optical system and reference optical system may be comprised of an optical fiber. This enables a small-size and inexpensive OCT apparatus.

Next, a few working examples of the present invention will be explained.

First Working Example

Referring to FIG. 1, an OCT apparatus according to the first working example will be explained.

FIG. 1 is a schematic diagram for explaining an optical system in the OCT apparatus of this working example.

Denoted in FIG. 1 at 100 is an OCT apparatus, and denoted at 103 and 113 are beam splitters. Denoted at 105 is a reference light, and denoted at 106 is a measuring light. Denoted at 107 is an eye to be examined, and denoted at 110 is a single mode fiber. Denoted at 111 and 120 are lenses, and denoted at 114 is a mirror.

Denoted at 115 is a dispersion compensation glass, and denoted at 119 is an XY scanner. Denoted at 122 is a balanced detector, and denoted at 123 is an amplifier. Denoted at 124 is a filter, and denoted at 125 is a personal computer (PC). Denoted at 126 a cornea of the eye to be examined, and denoted at 127 is a retina of the eye to be examined.

In this working example, the OCT apparatus 100 is used as a device for acquiring a tomogram of the retina 127 of the eye 107 to be examined.

The structure of the optical system in the OCT apparatus of this working example will be explained below.

First of all, the structure of the OCT apparatus 100 will be outlined.

FIG. 1 illustrates a conceptional diagram of the OCT apparatus 100 and, as a whole, a Mach-Zehnder interference system is constituted there.

In this diagram, light emitted from a light source 101 is split by a beam splitter 103-1 into a reference light 105 and a measuring light 106. The measuring light is reflected or scattered by the eye 107 to be observed, and it comes back from the eye as a returning light. After this, it is coupled with reference light 105 by means of a beam splitter 103-2.

After being coupled, the reference light 105 and the measuring light 106 are split by the beam splitter 103-2 and incident on a balanced detector 122. The balanced detector 122 converts a light intensity into a voltage. By using this signal, a tomogram of the eye 107 is produced.

Next, components around the light source 101 will be explained.

The light source 101 comprises an SLD (Super Luminescent Diode) which is a representative low coherent light source. It provides a wavelength of 830 nm and a bandwidth of 50 nm. Here, the bandwidth is an important parameter since it has an influence upon the resolving power of the tomogram in the optical axis direction, to be obtained.

As regards the type of the light source, although an SLD is chosen for the light source here, anyone that can provide low coherent light may be used. For example, an ASE (Amplified Spontaneous Emission) device may be used.

Furthermore, with regard to the wavelength, since an eye is to be measured, use of near infrared ray may be appropriate. Furthermore, since the wavelength has an influence on the crosswise resolving power of the tomogram to be obtained, use of shortest wavelength is desirable. A wavelength of 830 nm is used here. In dependence upon the measurement part of the observation object, any other wavelength may be chosen, as a matter of course.

The light emitted from the light source 101 is directed toward a lens 111-1 through a single mode fiber 110-1, and it is adjusted into a parallel light having a beam diameter of 4 mm.

Next, the light path for the reference light 105 which is an important feature of the present invention will be explained.

The reference light 105 divided by the beam splitter 103-1 is incident on the beam splitter 113-1, and it is split into a reference light 105-1 and a reference light 105-2. They are coupled with each other by means of the beam splitter 113-2, afterwards.

Here, denoted at 114-1 to 114-5 are mirrors, and denoted at 115-1 and 115-2 are dispersion compensation glasses. The length of the dispersion compensation glass 115-1 is L1 which is desirably made equal to a double of an ordinary eye depth. The dispersion compensation glass 115-1 functions to compensate the dispersion with respect to the reference light 105 when the measuring light 106 reciprocates in the eye 107.

In this example, L1=46 mm which is twofold of 23 mm corresponding to an average eye-ball diameter of Japanese people. Furthermore, the distance L2 between the beam splitter 113-1 and the mirror 114-1 has to be made slightly larger than or smaller than the depth of eye 107. In this example, L2=24 mm. However, it may be re-adjusted at the time of measurement.

As an important feature of this example, as a result there are two reference light paths, wherein the optical path length difference of the reference light 105-1 and 105-2 is 2L2=48 mm which is made slightly larger than the twofold of the ordinary eyeball depth.

Denoted at 117-1 and 117-2 are electric stages which are made movable in the directions as illustrated to control the optical path lengths of the reference light 105-1 and 105-2, independently.

Next, the manner how the reference light 105 is modulated will be explained.

Here, denoted at 116-1 and 116-2 are acousto-optic modulation devices, and denoted at 116-3 is a controller for the acousto-optic modulation devices. Here, the two acousto-optic modulation devices 116-1 and 116-2 are used as a shifter of the frequency of light.

The shifting frequencies of the acousto-optic modulation devices 116-1 and 116-2 are +41 MHz and −40 MHz, respectively. As a result of this, the frequency of the reference light 105 can be shifted by 1 MHz. Furthermore, the dispersion compensation glass 115-2 functions to provide dispersion compensation for the lenses 120-1 and 120-2 used for the scan of eye 107.

Next, the light path of the measuring light 106 will be explained.

The measuring light 106 divided by the beam splitter 103-1 is reflected by the beam splitter 103-3, and it is incident on a mirror of an X-Y scanner 119.

Here, for simply, the X-Y scanner 119 is illustrated as being a single mirror. Actually, however, two pieces of mirrors, comprising a mirror for X scan and a mirror for Y scan, are disposed juxtaposed to provide raster scan of the retina 127 in a direction perpendicular to the optical axis. Furthermore, the center of the measuring light 106 is so adjusted to be in alignment with the center of rotation of the mirror of X-Y scanner 119. The lenses 120-1 and 120-2 are an optical system for scanning the retina 127, and these have a function for transforming the measuring light 106 into a beam diameter suitable for the measurement of eye 107.

Here, the beam diameter is made equal to 6 mm. Also, the focal distances of the lens 120-1 and 120-2 are equal to 30 mm and 45 mm, respectively.

When the measuring light 106 is incident on the eye 107, because of the reflection at the surface of the cornea 126 and the retina 127, the measuring light 106 is divided by the beam splitter 103-2 and directed to the balanced detector 122.

Next, the structure of the measuring system in the OCT apparatus of this working example will be explained.

The OCT apparatus 100 can acquire a tomogram (an OCT image) which is comprised of the intensity of an interference signal provided by the Mach-Zehnder interference system.

This measuring system will be explained in detail. The measuring light 106 reflected by the retina 127 is then reflected by the X-Y scanner 119, and it is split by the beam splitter 103-2. On the other hand, the reference light 105 as well is divided by the beam splitter 103-2. Here, the reference light 105 and the measuring light 106 are so adjusted that these are coupled together behind the beam splitter 103-2.

Then, through the optical fibers 110-2 and 110-3, it is directed to the balanced detector 122, whereby the light intensity of the coupled reference light 105 and measuring light 106 is converted into a voltage. The thus obtained voltage signal is amplified by an amplifier 123, and a necessary frequency component is taken out by a filter 124. Then, decoding and data processing are carried out by the PC 125, whereby a tomogram is obtained.

Here, the reference light 105 has been frequency-shifted by 1 MHz as described hereinbefore. Therefore, the voltage signal obtained as described above provides a beat signal of 1 MHz. Although the measuring light 106 is generally very weak, since the reference light 105 is large, the detection sensitivity can be increased.

With regard to the filter 124, a bandpass filter of 1 MHz is used here. By cutting unnecessary frequency components, high sensitivity detection of the beat signal is accomplished.

Next, the manner how a tomogram is obtained using an OCT apparatus of this working example, will be explained.

In the OCT apparatus 100, by controlling the two electric stages 117-1 and 117-2 and the X-Y scanner 119, a tomogram of a desired portion of the retina 127 can be acquired. Here, the manner of acquiring a tomogram (along a plane parallel to the optical axis) of the retina 127 will be explained.

When the measuring light 106 is incident on the eye 107, due to reflections at various positions, the measuring light 106 reaches the balanced detector 122 with time delays corresponding to these positions.

Here, since the bandwidth of light source 101 is wide and the coherence length is short, an interference signal can be detected at the balanced detector 122 only when the optical path lengths of the reference light 105 and the measuring light 106 are equal to each other.

Since the frequency of the reference light 105 has been shifted by 1 MHz as described above, the interference signal will provide a beat signal of 1 MHz.

Furthermore, since the reference light 105 includes portions split into the reference light 105-1 and the reference light 105-2, there is a feature that an interference signal is obtained based on the reflections from the two positions of the measuring light 106.

Here, the whole of the reference light path including the reference light 105-1 is denoted by DL1, while the whole of the reference light path including the reference light 105-2 is denoted by LD2.

As described above, the optical path length difference between the reference light 105-1 and the reference light 105-2 is 2L2=48 mm, and it is made slightly larger than the twofold of an ordinary eyeball depth. Namely, the optical path length difference 2L2 between DL1 and DL2 has been adjusted so as to correspond to the reciprocal length of the depth of the eye 107. Hence, if DL1 is adjusted to detect reflection from the retina 127 while DL2 is adjusted to detect reflection from the cornea 126, both of the interference signal of the cornea 126 and the interference signal of the retina 127 can be acquired at the same time. It is to be noted that the words "at the same time" mentioned here do not mean exactly the same time with respect to the time base, but it means that the reflected signal from the cornea and the reflected signal from the retina are acquired in a time which is sufficiently short as compared with the motion of the eye being examined, during the measurement.

Figure 2A:
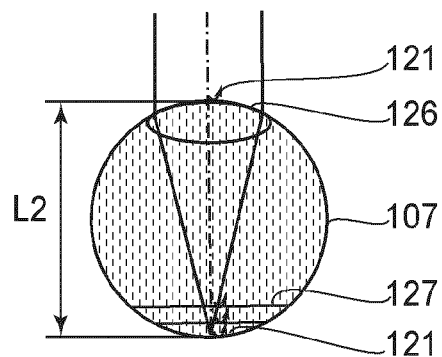
FIGS. 2A-2C are schematic diagrams for explaining the manner how a tomogram is acquired in the first working example of the present invention.
Figure 2B:
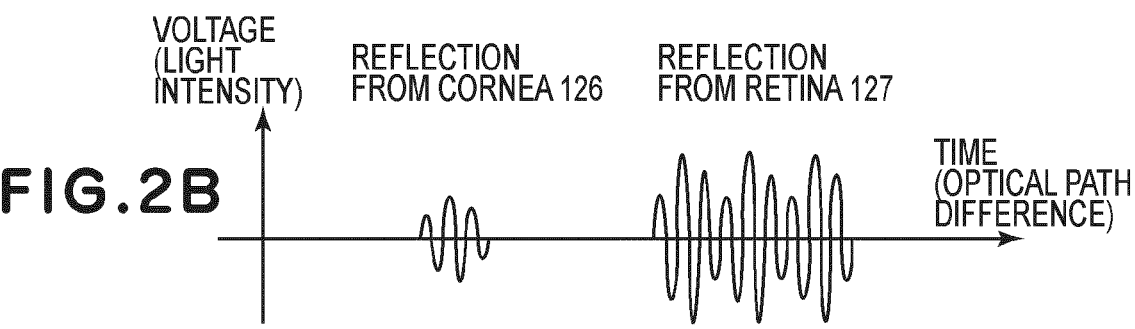
Figure 2C:
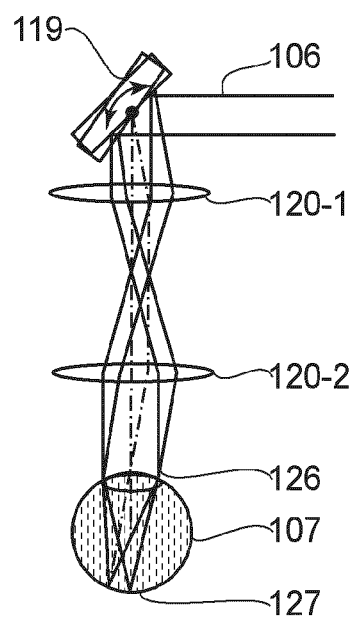

Next, the manner of adjusting the reference light paths DL1 and DL2 will be explained in more detail. FIGS. 2A-2C are diagrams for explaining the manner how the reference light path is adjusted in this working example. FIG. 2A shows that measuring light 106 which is a parallel light is incident on the eye 107 and it is reflected (reflected light 121) by each layer of the cornea surface 126 and retina 127.

First of all, by using the electric stages 117-1 and 117-2, the optical path length of the reference light paths DL1 and DL2 is adjusted so that the reference light 105-1 advancing along DL1 and the reflected light 121 from cornea 126 interfere with each other, and also that the reference light 105-2 advancing along DL2 and the reflected light 121 from the retina 127 interfere with each other. By moving the electric stages 117-1 and 117-2 while including the adjusted positions of them, a signal such as shown in FIG. 2B is detected at the balanced detector 122. The axis of ordinate represents the light intensity, and the axis of abscissas depicts time. If the electric stages 117-1 and 117-2 are moved at a constant speed, the axis of abscissas represents the position of the electric stages 117-1 and 117-2 and it can be regarded as the optical path length of the reference light path or measurement light path. In this example, FIG. 2B illustrates a case where the reflected lights from the cornea 126 and retina 127 do not overlap with each other with respect to time. However, it is possible that the reflected lights from the cornea 126 and retina 127 overlap with each other with respect to time. In consideration of this, the moving range of either of the electric stages 117-1 and 117-2 have to be changed so that the reflected lights from the cornea 126 and retina 127 are detected independently of each other with respect to time.

If the optical path length is adjusted by using 117 electric stages 117-1 and 117-2, the adjustment may be done so that the reflected light from the cornea 126 appears at the left-hand side on the time base as shown in FIG. 2B, while the reflected light from the retina 127 appears at the right-hand side. This relationship may be reversed, such that the reflected light from the cornea 126 appears at the left-hand side while the reflected light from the retina 127 appears at the right-hand side.

Next, the manner of acquiring a tomogram will be explained in more detail.

FIGS. 2A-2C are diagrams illustrating how a tomogram is acquired in this working example.

First of all, the X-Y scanner 119 is held fixed, and the electric stages 117-1 and 117-2 are adjusted using the above-mentioned adjustment method, so that DL1 detects the reflection from around the retina 127 while DL2 detects the reflection from around the surface of the cornea 126, independently of each other as interference signals. More specifically, a relation L2=24 mm is provided as described hereinbefore.

As shown in FIG. 2A, the measuring light 106 which is a parallel light is incident on the eye 107, and it is reflected (reflected light 121) by each layer of the cornea surface 126 and the retina 127.

Furthermore, if the electric stages 117-1 and 117-2 are moved at the same time, a signal such as shown in FIG. 2B is detected at the balanced detector 122. Thus, by slightly moving the electric stages 117-1 and 117-2, the information related to the cornea 126 and retina 127 is obtainable.

This signal is the beat signal mentioned hereinbefore. By squaring the amplitude thereof and decoding the same, a reflectivity distribution in the optical axis direction is provided.

Furthermore, as shown in FIG. 2C, if a similar operation is repeated with respect to arbitrary points on the retina 127 by using the X-Y scanner 119, a two-dimensional distribution of the reflectivity is provided, such that a tomogram of the cornea 126 and retina 127 is obtained by a single measurement.

For example, DL1 may be scanned in the optical axis direction (Z-direction), and this operation may be conducted with respect to arbitrary points in the X-axis direction by using the X-Y scanner 119. In that occasion, a tomogram such as shown in FIG. 3A may be provided.

The tomogram 130 is inherently a combination of sample reflectivities being disposed in an array. The reflectivities are displayed while being converted in terms of a gray scale. Here, only the boundaries of these are illustrated.

Next, a method of correcting the motion artifact using the OCT apparatus of this working example will be explained.

Figure 3A:
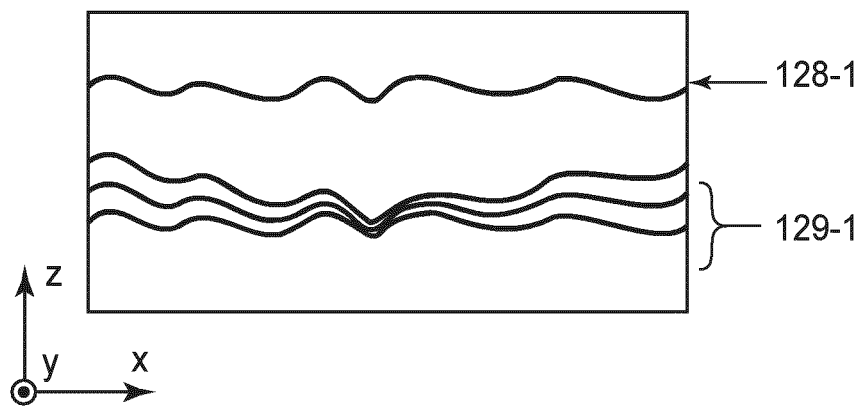
FIGS. 3A and 3B are schematic diagrams for explaining the manner how the motion artifact is corrected in the first working example of the present invention.
Figure 3B:
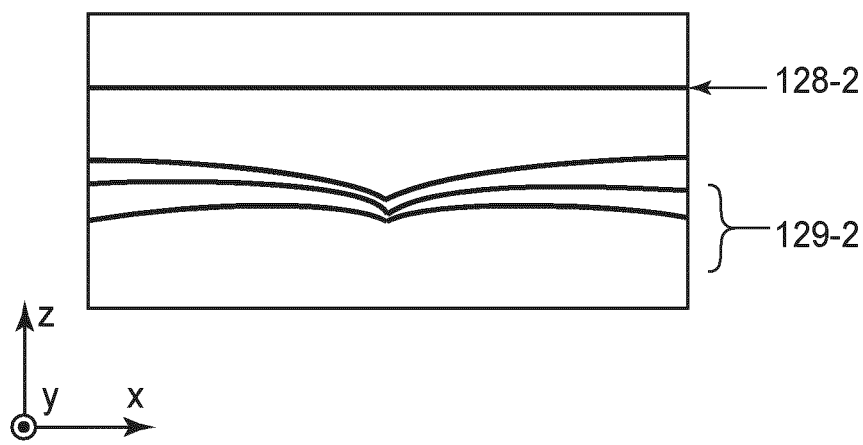

FIGS. 3A and 3B are diagrams for explaining the method of correcting the motion artifact in this working example.

In the tomogram 330 shown in FIG. 3A, there are a boundary 128-1 which is the surface of the cornea 126 and a boundary 129-1 which is the internal structure of the retina 127. Originally, if there is no motion of the eyeball 107 during the measurement, the measuring light 106 should be incident on a similar position of the cornea 126. Namely, the boundary 128-1 depicts the motion of the eyeball 107 in the optical axis direction.

Here, if correction is made by an amount corresponding to the displacement of the eyeball in the optical axis direction so that the boundary 129-2 is turned into a straight line with respect to the tomogram 330, a tomogram 331 as shown in FIG. 3B is provided, such that a tomogram of the retina 127 in which the motion artifact is reduced is obtained.

Thus, in this example, a boundary 128-2 being corrected into a straight line and a boundary 129-2 illustrating the internal structure of the retina are obtained.

Second Working Example

The second working example will be described with reference to a structural example wherein the light path of at least one of the inspection optical system, detection optical system and reference optical system described hereinbefore is comprised of an optical fiber.

Figure 4:
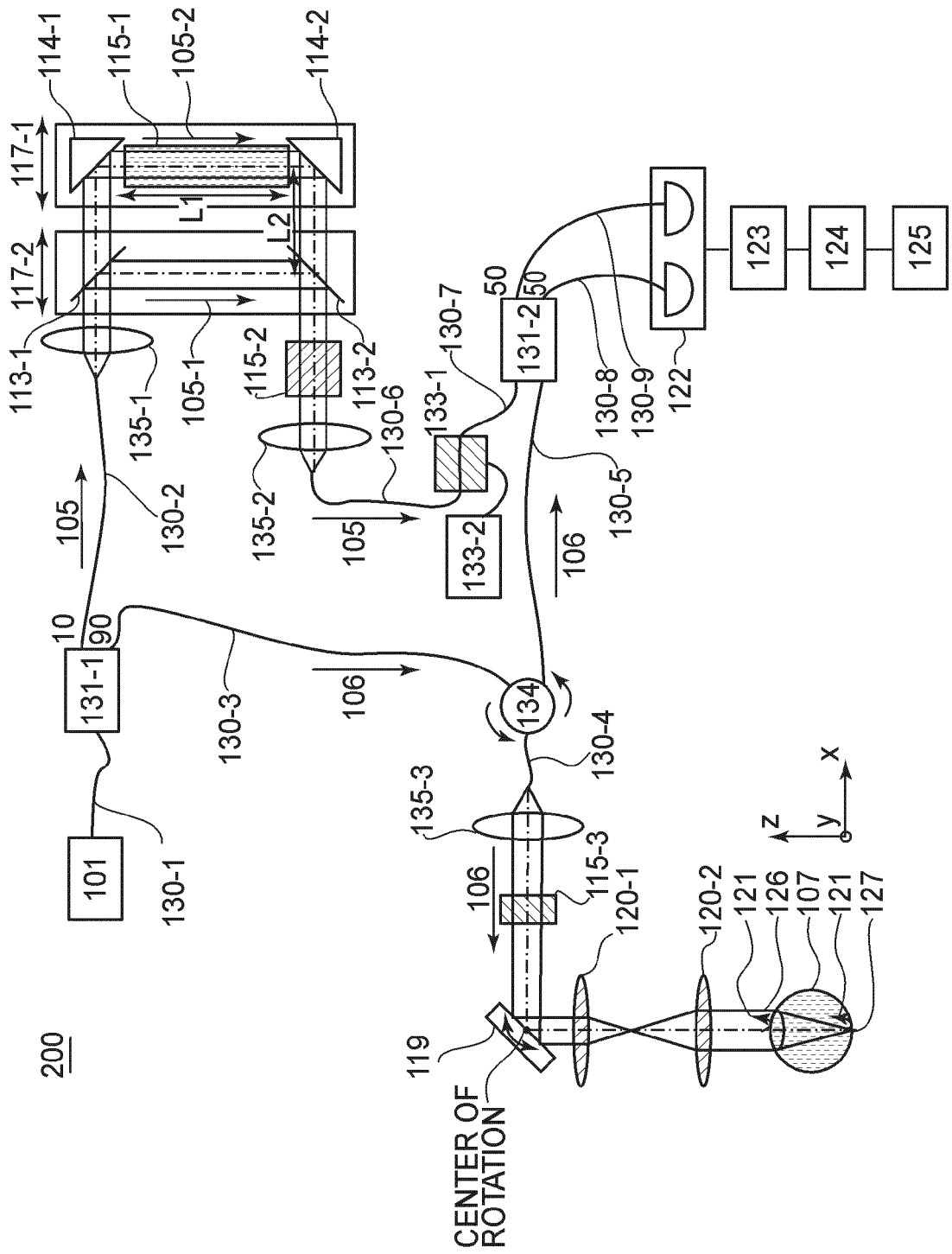
FIG. 4 is a schematic diagram for explaining the structure of an OCT apparatus according to a second working example of the present invention.

FIG. 4 is a schematic diagram for explaining the structure of the OCT apparatus in the second working example of the present invention.

In FIG. 4, like numerals are assigned to components similar or corresponding to those of the first working example illustrated in FIG. 1. Thus, description of the duplicated structure will be omitted.

In FIG. 4, denoted at 200 is an OCT apparatus, and denoted at 130 is a single mode fiber. Denoted at 131 is an optical coupler, and denoted at 134 is an optical circulator.

In this working example, the OCT apparatus 200 is used as a device for acquiring a tomogram of the retina 127 of an eye 107 to be examined. Furthermore, in this working example, by constituting a portion of the optical system using an optical fiber, reduction in size of the apparatus is accomplished. Except for the point that an optical fiber is used, the basic structure of this working example is the same as that of the first working example.

Next, the structure of the optical system in the OCT apparatus of this working example will be explained.

First of all, the structure of the OCT apparatus 200 will be outlined.

FIG. 4 illustrates a conceptional diagram of the OCT apparatus 200 and, as a whole, a Mach-Zehnder interference system is constituted there.

In FIG. 4, light emitted from a light source 101 is split into a measuring light 106 (90) and a reference light 105 (10) by means of an optical coupler 131-1 through a single mode fiber 130-1.

The measuring light 106 is reflected by the eye 107 which is an observation object and, after this, it is coupled with the reference light 105 by means of an optical coupler 131-2. After this, the light is split and is incident on a balanced detector 122.

By using the light intensity obtained by the balanced detector 122, a tomogram of the eye 107 is produced.

Next, the components around the light source 101 will be explained. The light source 101 itself is similar to that of the first working example. The light emitted from the light source 101 is directed through the single mode fiber 130-1 to the optical coupler 131-1 where it is split at an intensity ratio of 90:10. The thus split lights provide a measuring light 106 and a reference light 105, respectively.

Next, the light path of the reference light 105 which is one feature of this working example will be explained.

After the reference light 105 is split by the optical coupler 131-1, it is directed through the single-mode fiber 130-2 toward a lens 135-1 by which the light is adjusted into a parallel light having a beam diameter of 4 mm. The electric stages 117-1 and 117-2, mirrors 114-1 and 114-2 annexed to it, beam splitters 113-1 and 113-2, dispersion compensation glass 115-1 are all similar to those of the first working example, description of these components will be omitted. The thus coupled reference light 105 goes through the dispersion compensation glass 115-2 and, thereafter, it is directed to the single mode fiber 130-6 through the lens 135-2.

After this, the light goes through an acousto-optic modulation device 133-1 and a single-mode fiber 130-7, and it is incident on an optical coupler 131-2.

The acousto-optic modulation device 133-1 is for the optical fiber, and it functions to provide a frequency shift of 1 MHz while using a controller 133-2. Thus, the reference light 105 provided there is similar to that of the first working example.

Next, the light path of the measuring light 106 will be explained. The measuring light 106 divided by the optical coupler 131-1 goes through a single mode fiber 130-3, and it is incident on an optical circulator 134.

Afterwards, it goes through a single mode fiber 130-4, and then it is directed to a lens 135-3 by which the light is adjusted into a parallel light having a beam diameter of 4 mm. Furthermore, after passing through a dispersion compensation glass 115-3, the light is incident on a mirror of the X-Y scanner 119.

Since the optical system between from the X-Y scanner 119 to the eye 107 is similar to that of the first working example, description thereof will be omitted.

Here, the dispersion compensation glass 115-3 functions to compensate for the dispersion of the acousto-optic modulation device 133-1.

In this example, since the measuring light 106 reciprocally goes through the dispersion compensation glass 115-2, the thickness of the dispersion compensation glass 115-2 is made equal to a half of the glass thickness of the acousto-optic modulation device 133-1.

When the measuring light 106 is incident on the eye 107, due to the reflection at the surface of the cornea 126 and the retina 127 as well as the internal reflection, the measuring light 106 goes through the optical circulator 134 and is directed to the optical coupler 131-2.

Next, the structure of the measuring system in the OCT apparatus of this working example will be explained next.

The OCT apparatus 200 can acquire a tomogram (an OCT image) which is comprised of the intensity of an interference signal provided by the Mach-Zehnder interference system. This measuring system will be explained in detail. The measuring light 106 reflected by the retina 127 is then reflected by the X-Y scanner 119. Then, it is coupled with the reference light 105 by means of the optical coupler 131-2 and, subsequently, it is divided by a ratio of 50:50. Thereafter, the lights go through single mode fibers 130-8 and 130-9 and directed to a balanced detector 122.

The light intensity of the coupled reference light 105 and measuring light 106 is converted into a voltage. The thus obtained voltage signal is amplified by an amplifier 123, and a necessary frequency component is taken out by a filter 124. Then, decoding and data processing are carried out by the PC 125, whereby a tomogram is obtained.

Next, the manner how a tomogram is obtained using an OCT apparatus of this working example, will be explained. In the OCT apparatus 200, by controlling the two electric stages 117-1 and 117-2 and the X-Y scanner 119, a tomogram of a desired portion of the retina 127 can be acquired. Since details of the manner of acquiring a tomograph are similar to the first working example, description will be omitted here.

Next, the manner how the motion artifact is corrected using the OCT apparatus of this working example, will be explained. The OCT apparatus 200 has a function for correcting the motion artifact, as one feature. Since details of correcting the motion artifact as well are similar to the first working example, description will be omitted here.

While the invention has been described with reference to the structures disclosed herein, it is not confined to the details set forth and this application is intended to cover such modifications or changes as may come within the purposes of the improvements or the scope of the following claims.

This application claims priority from Japanese Patent Application No. 2007-260855 filed Oct. 4, 2007, for which is hereby incorporated by reference.

What is claimed is:

1. An optical coherence tomographic apparatus for obtaining a tomographic image of an eye based on an interference light by interfering a returning light which returns from the eye irradiated by a measuring light with a reference light corresponding to the measuring light, the optical coherence tomographic apparatus comprising:
    a scanning unit configured to scan the measuring light on a retina of the eye and provided at a position substantially conjugate with a cornea of the eye;
    a reference light path configured to include at least a first reference light path and a second reference light path, wherein the second reference light path has an optical path length shorter than that of the first reference light path;
    a first acquisition unit configured to acquire a first tomographic image of the retina using the first reference light path;
    a second acquisition unit configured to acquire a second tomographic image of the cornea using the second reference light path; and
    a correction unit configured to correct a positional deviation of the first tomographic image in a depth direction of the eye by changing the cornea in the second tomographic image to a substantially linear line extending in a direction perpendicular to the depth direction.

2. The optical coherence tomographic apparatus according to claim 1, further comprising:
    a reference optical path length control unit configured to independently control reference optical path lengths of the first reference light path and the second reference light path;
    a first stage unit, provided in the first reference light path, configured to change the reference optical path length of the first reference light path;
    a second stage unit, provided in the second reference light path, configured to change the reference optical path length of the second reference light path;
    a first splitter unit and a second splitter unit provided in the reference light path and on the second stage unit.

3. The optical coherence tomographic apparatus according to claim 2, wherein said reference optical path length control unit adjusts the reference optical path lengths of the first reference light path and the second reference light path so that the first tomographic image and the second tomographic image are separated from each other with respect to time.

4. The optical coherence tomographic apparatus according to claim 3, wherein the adjustment by said reference optical path length control unit is performed automatically.

5. The optical coherence tomographic apparatus according to claim 1, further comprising:
    a detecting unit configured to detect a light intensity and to convert it into an electrical signal, so as to detect a signal based on the interference light; and
    an image forming unit configured to perform an arithmetic operation to the electrical signal to obtain an image.

6. The optical coherence tomographic apparatus according to claim 1, further comprising:
    a branching unit configured to branch from a common reference optical path into the first reference optical path and the second reference optical path; and
    a dispersion compensation unit, provided in the branched-out first reference optical path, configured to compensate for ophthalmic dispersion of the eye.

7. The optical coherence tomographic apparatus according to claim 1, further comprising:
- an inspection optical system configured to direct the returning light from the object to be inspected toward the detection position;
- a detection optical system configured to direct the measuring light toward the object to be inspected, through the measurement light path; and
- a reference optical system configured to direct the reference light toward the detection position,
- wherein a light path of at least one of said inspection optical system, said detection optical system, and said reference optical system is comprised of an optical fiber.

8. The optical coherence tomographic apparatus according to claim 1, further comprising a display unit configured to display the corrected tomographic image.

9. An optical coherence tomographic apparatus according to claim 1, further comprising a branching unit configured to branch from a common optical path into the first reference light path and the second reference light path, and a reference optical path length control unit configure to move said branching unit in a direction of an optical axis of the common reference optical path.

10. An optical coherence tomographic apparatus comprising:
- an optical system configured so that light from a light source is split into a measuring light and a reference light, wherein the reference light interferes with a returning light of the measuring light returning from an object, and wherein a tomographic image of the object is obtained based on the interference light;
- a reference light path configured to include at least a first reference light path and a second reference light path, wherein the second reference light path has an optical path length shorter than that of the first reference light path; and
- a reference optical path length control unit configured to independently control reference optical path lengths of the first reference light path and the second reference light path;
- a first stage unit, provided in the first reference light path, configured to change the reference optical path length of the first reference light path;
- a second stage unit, provided in the second reference light path, configured to change the reference optical path length of the second reference light path; and
- a first splitter unit and a second splitter unit provided in the reference light path and on the second stage unit.

11. The optical coherence tomographic apparatus according to claim 10, further comprising:
- an acquisition unit configured to acquire first tomographic information of the object at a first inspection position based on the interference light using the first reference light path, and second tomographic information of the object at a second inspection position based on the interference light using the second reference light path, wherein the second inspection position is shallower than the first inspection position with respect to a depth direction of the object,
- wherein the first tomographic information and the second tomographic information are related with each other with respect to a positional relationship in the depth direction, and
- wherein the positional relationship in the depth direction between the first tomographic information and the second tomographic information corresponds to a positional relationship between the first inspection position and the second inspection position with respect to the depth direction.

12. The optical coherence tomographic apparatus according to claim 11, wherein, with respect to the positional relationship in the depth direction, a positional gap occurring in at least a tomography image of the object to be examined which comprises the first tomographic information and the second tomographic information, is corrected based on the second tomographic information.

13. The optical coherence tomographic apparatus according to claim 10, further comprising:
- an acquisition unit configured to acquire first tomographic information of the object at a first inspection position based on the interference light using the first reference light path, and second tomographic information of the object at a second inspection position based on the interference light using the second reference light path, wherein the second inspection position is shallower than the first inspection position with respect to a depth direction of the object, and
- wherein at least a tomograph image of the object to be inspected in the depth direction is produced with a positional gap of the second tomographic information in the depth direction being compensated, based on information about said second inspection position.

14. The optical coherence tomographic apparatus according to claim 11,
- wherein, as the first tomographic information, a first reference optical system for acquiring a retina tomographic image of an eye to be examined is comprised of the first reference light path,
- wherein, as the second tomographic information, a second reference optical system for acquiring a cornea tomographic image of the eye to be examined is comprised of the second reference light path, and
- wherein, when the retina tomographic image is made, a positional deviation of the retina tomographic image is corrected based on the second tomographic information including information about the position of the cornea, thereby to reduce motion artifact.

15. The optical coherence tomographic apparatus according to claim 14, wherein the first reference light path and the second reference light path have an optical path length difference of not less than 30 mm and not greater than 60 mm.

16. The optical coherence tomographic apparatus according to claim 14, further comprising:
- a branching unit configured to branch from a common optical path into the first reference optical path and the second reference optical path; and
- a dispersion compensation unit, provided in the branched-out first reference optical path, configured to compensate for ophthalmic dispersion of the eye.

17. The optical coherence tomographic apparatus according to claim 14, further comprising:
- a scanning unit configured to scan the measuring light on the retina and provided at a position substantially conjugate with the cornea; and
- a correcting unit configured to correct a position, with respect to a direction of an optical path of the measuring light, of the optical coherence tomographic image of the cornea to a predetermined position.

18. The optical coherence tomographic apparatus according to claim 14, further comprising:
- a scanning unit configured to scan the measuring light on the retina and provided at a position substantially conjugate with the cornea; and a correcting unit configured to correct the optical coherence tomographic image of the retina by changing a position of the optical coherence tomographic image of the cornea to a substantially linear line extending in a direction perpendicular to the optical path of the measuring light.

19. An optical coherence tomographic system for obtaining a tomographic image of an eye based on an interference light by interfering a returning light which returns from the eye irradiated by a measuring light with a reference light corresponding to the measuring light, the optical coherence tomographic apparatus comprising:

a scanning unit configured to scan the measuring light on a retina of the eye and provided at a position substantially conjugate with a cornea of the eye;

a reference light path configured to include at least a first reference light path and a second reference light path, wherein the second reference light path has an optical path length shorter than that of the first reference light path;

a first acquisition unit configured to acquire a first tomographic image of the retina using the first reference light path; and a second acquisition unit configured to acquire a second tomographic image of the cornea using the second reference light path; and a correction unit configured to correct a positional deviation of the first tomographic image in a depth direction of the eye by changing the cornea in the second tomographic image to a substantially linear line extending in a direction perpendicular to the depth direction.

20. The system according to claim 19, further comprising a display unit configured to display the corrected tomographic image.

21. An optical coherence tomographic system according to claim 19, further comprising a branching unit configured to branch from a common optical path into the first reference light path and the second reference light path, and a reference optical path length control unit configure to move said branching unit in a direction of an optical axis of the common reference optical path.

22. An ophthalmologic system comprising:

a scanning unit configured to scan a measuring light on a retina of the eye and provided at a position substantially conjugate with a cornea of the eye;

a first obtain unit that obtains an optical coherence tomographic image of the cornea using a first interference light by interfering a returning light which returns from the cornea with reference light from a first reference light path having an optical path length corresponding to a position of the cornea;

a second obtain unit that obtains an optical coherence tomographic image of the retina using a second interference light by interfering a returning light which returns from the retina with reference light from a second reference light path having an optical path length corresponding to a position of the retina; and a correction unit that corrects a positional deviation of the optical coherence tomographic image of the retina in a depth direction of the eye by changing the cornea in the optical coherence tomographic image of the cornea to a substantially linear line extending in a direction perpendicular to the depth direction.

23. The ophthalmologic system according to claim 22, wherein the first reference light path having the optical path length corresponding to the position of the cornea and the second reference light path having the optical path length corresponding to the position of the retina are partly common.

24. The ophthalmologic system according to claim 22, further comprising a display unit configured to display the corrected tomographic image.

25. An optical coherence tomographic system according to claim 22, further comprising:

a branching unit configured to branch from a common optical path into the first reference light path and the second reference light path, and a reference optical path length control unit configure to move said branching unit in a direction of an optical axis of the common reference optical path; and a dispersion compensation unit, provided in the first reference optical path, configured to compensate ophthalmic dispersion of the eye.

* * * * *